United States Patent
Belcher et al.

(10) Patent No.: US 12,392,782 B2
(45) Date of Patent: Aug. 19, 2025

(54) CHARACTERIZATION OF PROTEIN BINDING TO PER- AND POLYFLUOROALKYL SUBSTANCES

(71) Applicant: North Carolina State University, Raleigh, NC (US)

(72) Inventors: Scott M. Belcher, Raleigh, NC (US); Thomas W. Jackson, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 818 days.

(21) Appl. No.: 17/704,825

(22) Filed: Mar. 25, 2022

(65) Prior Publication Data
US 2022/0308064 A1 Sep. 29, 2022

Related U.S. Application Data

(60) Provisional application No. 63/166,606, filed on Mar. 26, 2021.

(51) Int. Cl.
*G01N 33/68* (2006.01)
*G01N 33/58* (2006.01)

(52) U.S. Cl.
CPC ........... *G01N 33/68* (2013.01); *G01N 33/582* (2013.01)

(58) Field of Classification Search
CPC ... G01N 33/68; G01N 33/582; G01N 33/6803
See application file for complete search history.

(56) References Cited

U.S. PATENT DOCUMENTS

2022/0404281 A1* 12/2022 Atwood ............... G01N 33/587

OTHER PUBLICATIONS

Liu et al., Characterization of the binding of per- and polyfluorinated substances to proteins: A methodological review, Trends in Analytical Chemistry 116 (2019) 177-185 (Year: 2019).*
Beesoon et al., Isomer-Specific Binding Affinity of Perfluorooctanesulfonate (PFOS) and Perfluorooctanoate (PFOA) to Serum Proteins. Environ Sci Technol. May 5, 2015;49(9):5722-31.
Bischel et al., Noncovalent interactions of long-chain perfluoroalkyl acids with serum albumin. Environ Sci Technol. Jul. 1, 2010;44(13):5263-9.
Bowman. Fluorotechnology Is Critical to Modern Life: The FluoroCouncil Counterpoint to the Madrid Statement. Environ. Health Perspect. 2015. 123, A112-113.
Brusseau et al., PFAS concentrations in soils: Background levels versus contaminated sites. Sci Total Environ. Oct. 20, 2020;740:140017. 23 Pages.
Buck et al., Perfluoroalkyl and polyfluoroalkyl substances in the environment: terminology, classification, and origins. Integr Environ Assess Manag. Oct. 2011;7(4):513-41.
Chen et al., Fluorescence study on site-specific binding of perfluoroalkyl acids to human serum albumin. Arch Toxicol. Mar. 2009;83(3):255-61.

(Continued)

*Primary Examiner* — Jennifer Wecker
*Assistant Examiner* — Steven Ray Castaneda
(74) *Attorney, Agent, or Firm* — Casimir Jones, S.C.; Anne M. Reynolds

(57) ABSTRACT

Disclosed herein are compositions and methods for characterizing protein binding to per- and polyfluoroalkyl substances (PFAS).

19 Claims, 5 Drawing Sheets

(56) References Cited

OTHER PUBLICATIONS

Cheng et al., A Permeability-Limited Physiologically Based Pharmacokinetic (PBPK) Model for Perfluorooctanoic acid (PFOA) in Male Rats. Environ Sci Technol. Sep. 5, 2017;51(17):9930-9939.
Cheng et al., Predicting Relative Protein Affinity of Novel Per- and Polyfluoroalkyl Substances (PFASs) by An Efficient Molecular Dynamics Approach. Environ Sci Technol. Jul. 17, 2018;52(14):7972-7980.
Curry. Plasma albumin as a fatty acid carrier. Advances in Molecular and Cell Biology, 2003, vol. 33 29-46.
Epps et al., The ligand affinity of proteins measured by isothermal denaturation kinetics. Anal Biochem. May 1, 2001;292(1):40-50.
Ericsson et al., Thermofluor-based high-throughput stability optimization of proteins for structural studies. Anal Biochem. Oct. 15, 2006;357(2):289-98.
Forsthuber et al., Albumin is the major carrier protein for PFOS, PFOA, PFHxS, PFNA and PFDA in human plasma. Environ Int. Apr. 2020;137:105324. 5 pages.
Fourth Meeting of the Conference of the Parties of the Stockholm Convention. 2009. 112 pages.
Gao et al., Theory and applications of differential scanning fluorimetry in early-stage drug discovery. Biophys Rev. Feb. 2020;12(1):85-104.
Guillette et al., Elevated levels of per- and polyfluoroalkyl substances in Cape Fear River Striped Bass (Morone saxatilis) are associated with biomarkers of altered immune and liver function. Environ Int. Mar. 2020;136:105358. 23 pages.
Han et al., Binding of perfluorooctanoic acid to rat and human plasma proteins. Chem Res Toxicol. Jun. 2003;16(6):775-81.
Hebert et al., Development of a fluorescence model for the binding of medium- to long-chain perfluoroalkyl acids to human serum albumin through a mechanistic evaluation of spectroscopic evidence. Anal Chem. Aug. 1, 2010;82(15):6463-71.
Honoré et al., Detection of carrier heterogeneity by rate of ligand dialysis: medium-chain fatty acid interaction with human serum albumin and competition with chloride. Anal Biochem. May 15, 1988;171(1):55-66.
Houde et al., Monitoring of perfluorinated compounds in aquatic biota: an updated review. Environ Sci Technol. Oct. 1, 2011;45(19):7962-73.
Kotlarz et al., Measurement of Novel, Drinking Water-Associated PFAS in Blood from Adults and Children in Wilmington, North Carolina. Environ Health Perspect. Jul. 2020;128(7):77005. 12 pages.
Layton et al., Quantitation of protein-protein interactions by thermal stability analysis. Protein Sci. Aug. 2011;20(8):1439-50.
Lee et al., Location of the medium chain fatty acid site on human serum albumin. Residues involved and relationship to the indole site. J Biol Chem. Jul. 10, 1980;255(13):6121-7.
Liberatore et al., Solvent Suitability for HFPO-DA ("GenX" Parent Acid) in Toxicological Studies. Environ Sci Technol Lett. May 18, 2020;7(7):477-481.
Liu et al., Weak polar interactions confer albumin binding site selectivity for haloether anesthetics. Anesthesiology. Apr. 2005;102(4):799-805.
Lo et al., Evaluation of fluorescence-based thermal shift assays for hit identification in drug discovery. Anal Biochem. Sep. 1, 2004;332(1):153-9.
Matulis et al., Thermodynamic stability of carbonic anhydrase: measurements of binding affinity and stoichiometry using ThermoFluor. Biochemistry. Apr. 5, 2005;44(13):5258-66.
Ng et al., Exploring the Use of Molecular Docking to Identify Bioaccumulative Perfluorinated Alkyl Acids (PFAAs). Environ Sci Technol. Oct. 20, 2015;49(20):12306-14.
Niesen et al., The use of differential scanning fluorimetry to detect ligand interactions that promote protein stability. Nat Protoc. 2007;2(9):2212-21.
Organisation for Economic Co-operation and Development. Toward a New Comprehensive Global Database of Per-and Polyfluoroalkyl Substances (PFASs): Summary Report on Updating the OECD 2007 List of Per-and Polyfluoroalkyl Substances (PFASs) (2018) 3 pages.
Organization for Economic Co-operation and Development (OECD). Results of the 2006 OECD Survey on Production and Use of PFOS, PFAS, PFOA, PFCA, Their Related Substances and Products/Mixtures Containing These Substances. (2006). 20 pages.
Prevedouros et al., Sources, fate and transport of perfluorocarboxylates. Environ Sci Technol. Jan. 1, 2006;40(1):32-44.
Ràfols et al., Molecular interactions between some non-steroidal anti-inflammatory drugs (NSAID's) and bovine (BSA) or human (HSA) serum albumin estimated by means of isothermal titration calorimetry (ITC) and frontal analysis capillary electrophoresis (FA/CE). Talanta. Dec. 2014;130:241-50.
Ràfols et al., Molecular interactions between warfarin and human (HSA) or bovine (BSA) serum albumin evaluated by isothermal titration calorimetry (ITC), fluorescence spectrometry (FS) and frontal analysis capillary electrophoresis (FA/CE). J Pharm Biomed Anal. Feb. 20, 2018;150:452-459.
Ren et al., Binding interactions of perfluoroalkyl substances with thyroid hormone transport proteins and potential toxicological implications. Toxicology. 2016; 366-367: 32-42.
Sabín et al., Effects of fluorinated and hydrogenated surfactants on human serum albumin at different pHs. Biomacromolecules. Jan. 2006;7(1):176-82.
Salvalaglio et al., Determination of energies and sites of binding of PFOA and PFOS to human serum albumin. J Phys Chem B. Nov. 25, 2010;114(46):14860-74.
Savitzky et al., Smoothing and Differentiation of Data by Simplified Least Squares Procedures. Anal. Chem. 1964. 36, 1627-1639.
Senisterra et al., Screening for ligands using a generic and high-throughput light-scattering-based assay. J Biomol Screen. Dec. 2006;11(8):940-8.
Senisterra et al., Thermal denaturation assays in chemical biology. Assay Drug Dev Technol. Apr. 2012;10(2):128-36.
Simeonov. Recent developments in the use of differential scanning fluorometry in protein and small molecule discovery and characterization. Expert Opin Drug Discov. Sep. 2013;8(9):1071-82.
Spector, Fatty acid binding to plasma albumin. J Lipid Res. May 1975; 16(3):165-79.
Takehara et al., Binding properties of Hydrophobic Molecules to Human Serum Albumin Studied by Fluorescence Titration. Anal. Sci. Int. J. Jpn. Soc. Anal. Chem. 2009; 25, 115-120.
Vedadi et al., Chemical screening methods to identify ligands that promote protein stability, protein crystallization, and structure determination. Proc Natl Acad Sci U S A. Oct. 24, 2006;103(43):15835-40.
Vivoli et al., Determination of protein-ligand interactions using differential scanning fluorimetry. J Vis Exp. Sep. 13, 2014;(91):51809. 13 pages.
Vorum et al., Fatty acid and drug binding to a low-affinity component of human serum albumin, purified by affinity chromatography. Int J Pept Protein Res. Nov. 1992;40(5):415-22.
Wang et al., Global emission inventories for C4-C14 perfluoroalkyl carboxylic acid (PFCA) homologues from 1951 to 2030, part II: the remaining pieces of the puzzle. Environ Int. Aug. 2014;69:166-76.
Wu et al., Interaction of perfluorooctanoic acid with human serum albumin. BMC Struct Biol. May 14, 2009;9:31. 7 pages.

* cited by examiner

CHARACTERIZATION OF PROTEIN BINDING TO PER- AND POLYFLUOROALKYL SUBSTANCES

CROSS-REFERENCE TO RELATED APPLICATIONS

This application claims priority to and the benefit of U.S. Provisional Patent Application No. 63/166,606, filed Mar. 26, 2021, the entire contents of which are incorporated herein by reference.

STATEMENT REGARDING FEDERALLY SPONSORED RESEARCH

This invention was made with government support under grant number ES031009 awarded by the National Institutes of Health. The government has certain rights in the invention.

TECHNICAL FIELD

Disclosed herein are compositions and methods for characterizing protein binding to per- and polyfluoroalkyl substances (PFAS).

BACKGROUND

PFAS are a large class of persistent man-made chemicals used in a wide variety of industrial and consumer applications. The poly- and perfluorinated aliphatic backbones of PFAS are hydrophobic, chemically inert, and thermally stable; consequently, they are persistent and accumulate in the environment and in biota (see, e.g., Houde et al. Environ. Sci. Technol. 45, 7962-7973 (2011)). A recent comprehensive analysis by the Organization of Economic Cooperation and Development identified>4,730 PFAS-related CAS registry numbers, including 947 compounds that were registered in the EPA Toxic Substances Control Act (TSCA) chemical inventory (Organisation for Economic Co-operation and Development. Toward a New Comprehensive Global Database of Per- and Polyfluoroalkyl Substances (PFASs): Summary Report on Updating the OECD 2007 List of Per- and Polyfluoroalkyl Substances (PFASs) (2018)).

In 2002, manufacturers in the United States began to phase out long-chain perfluoroalkyl acids (PFAAs) due to their persistence and toxicity. Short-chain PFAS are increasingly used as replacements in many applications and processes. Common examples of these replacements include perfluoroalkylcarboxylic acids (PFCAs) and perfluoroalkylsulfonic acids (PFSAs) with shorter fluoroalkyl chains (e.g., perfluorobutanoic acid (PFBA) and perfluorobutanesulfonic acid (PFBS)), per- and polyfluoroalkylethers (PFAEs), per- and polyfluoroalkyl ether acids (PFEAs) that contain one or more ether moieties (e.g., hexafluoropropylene oxide dimer acid (HFPO-DA)), and fluorotelomer acids and alcohols with perfluoroalkyl length≤six (see, e.g., Bowman, Environ. *Health Perspect.* 123, A112-113 (2015)). Since their introduction, shorter chain replacement PFAS are now detected ubiquitously in the environment and are accumulating in people and other organisms across the world (see, e.g., Guillette et al. *Environ. Int.* 136, 105358 (2020); Kotlarz et al. *Environ. Health Perspect.* 128, 77005 (2020); Brusseau et al. *Sci. Total Environ.* 740, 140017 (2020)).

There are only limited data available for the majority of known PFAS, including most of the replacement PFAS currently in use. The thousands of PFAS for which there is a paucity of available data necessitates the use of high throughput and predictive computational strategies to characterize the physiochemical properties, bioactivity, and potential toxicity across different classes of PFAS. Recently, physiologically-based pharmacokinetic and molecular dynamics modeling, quantitative structure-activity relationship, and machine learning approaches have been developed to predict protein binding affinity for PFAS (Cheng et al. *Environ. Sci. Technol.* 51, 9930-9939 (2017); Cheng et al. Environ. Sci. Technol. 52, 7972-7980 (2018)). However, the predictive capabilities of these approaches are currently limited by a lack of data defining fundamental physiochemical and toxicokinetic properties for most PFAS.

SUMMARY

In one aspect, disclosed herein is a method comprising:
(a) providing a first composition comprising a polyfluoroalkyl substance, an environment-sensitive fluorophore, a protein, and an aqueous buffer solution, and determining a melting temperature ($T_m$) for the protein in the first composition;
(b) providing a second composition comprising the environment-sensitive fluorophore, the protein, and the aqueous buffer solution, and determining a melting temperature ($T_m$) for the protein in the second composition; and
(c) calculating the difference between the $T_m$ of the protein in the first composition and the $T_m$ of the protein in the second composition ($\Delta T_m$).

In some embodiments, the method further comprises:
(d) providing N additional compositions, each of which comprises the environment-sensitive fluorophore, the protein, the polyfluoroalkyl substance, and the aqueous buffer solution, wherein N is at least 2, and determining a melting temperature ($T_m$) for the protein in each composition, wherein each additional composition comprises the polyfluoroalkyl substance at a different concentration; and
(e) for each of the N additional compositions, calculating the difference between the $T_m$ of the protein in the first composition and the $T_m$ of the protein in the additional composition ($\Delta T_m$).

In some embodiments, the method further comprises:
(f) plotting the $\Delta T_m$ for each composition against the concentration of the polyfluoroalkyl substance, and fitting the data to the following equation:

$$Y = \text{Bottom} + \frac{(\text{Top} - \text{Bottom}) * \left(1 - \left(P - Kd - X + \sqrt{(P + X + Kd)^2 - (4*P*X)}\right)\right)}{2*P}$$

wherein:
Top is maximal response;
Bottom is minimal response;
P is protein concentration;
$K_d$ is dissociation constant;
X is polyfluoroalkyl substance concentration; and
Y is $\Delta T_m$;
to thereby determine the dissociation constant for the polyfluoroalkyl substance and the protein.

In some embodiments, the method further comprises:
(g) plotting the $\Delta T_m$ for each composition against the log-transformed concentration of the polyfluoroalkyl substance, and fitting the data to the following equation:

$$Y = \text{Bottom} + \frac{(\text{Top} - \text{Bottom})}{1 + 10^{\wedge}((\text{Log}EC50 - X) * \text{HillSlope}}$$

wherein:
Top is maximal response;
Bottom is minimal response;
Log $EC_{50}$ is the log-transformed half-maximal effective concentration;
X is ligand concentration;
HillSlope is the Hill coefficient; and
Y is $\Delta T_m$.

In some embodiments, each $T_m$ is determined by differential scanning fluorimetry.

In some embodiments, each composition is contained within a well of a 96- or 384-well plate.

In some embodiments, the environment-sensitive fluorophore is selected from 9-(2-carboxy-2-cyanovinyl)julolidine, 9-(2,2-dicyanovinyl)julolidine, 4-(4-(dimethylamino)styryl)-N-methylpyridinium iodide, and GloMelt™ dye.

In some embodiments, the protein is selected from albumins, fatty acid binding proteins, immunoglobulins, peroxisome proliferator-activated receptors, and thyroid proteins. In some embodiments, the protein is selected from human serum albumin, bovine serum albumin, porcine serum albumin, rat serum albumin, rabbit serum albumin, and immunoglobulin G.

In some embodiments, the aqueous buffer solution comprises 4-(2-hydroxyethyl)-1-piperazineethanesulfonic acid.

In some embodiments, the polyfluoroalkyl substance is a perfluoroalkylcarboxylic acid, a perfluoroalkylsulfonic acid, a fluorotelomer carboxylic acid, a fluorotelomer sulfonic acid, a fluorotelomer alcohol, a polyfluoroalkyl ether acid, or a perfluoroalkyl ether acid. In some embodiments, the polyfluoroalkyl substance has a formula:

PFA-X wherein:
PFA is a polyfluoroalkyl group or a polyfluoroheteroalkyl group; and
X is selected from the group consisting of —COOH, —SO$_3$H, —OH, —SO$_2$NH$_2$, —OC(O)CH=CH$_2$, —OC(O)C(CH$_3$)=CH$_2$, and —CF$_3$.

In some embodiments, PFA is a $C_1$-$C_{12}$ polyfluoroalkyl group or a $C_1$-$C_{12}$ polyfluoroheteroalkyl group. In some embodiments, PFA is a $C_1$-$C_{12}$ perfluoroalkyl group or a $C_1$-$C_{12}$ perfluoroheteroalkyl group. In some embodiments, PFA has a formula: —(CF$_2$)$_n$CF$_3$, wherein n is 1, 2, 3, 4, 5, 6, 7, 8, 9, 10, or 11. In some embodiments, PFA has a formula: —(CH$_2$)$_2$(CF$_2$)$_n$CF$_3$, wherein n is 1, 2, 3, 4, 5, 6, 7, 8, or 9. In some embodiments, PFA has a formula: —(CR$^{a1}$R$^{b1}$)$_m$—O—(CR$^{a2}$R$^{b2}$CR$^{a3}$R$^{b3}$O)$_p$—(CR$^{a4}$R$^{b4}$)$_q$—CF$_3$, wherein: m is 1 or 2; p is 0, 1, or 2; q is 0, 1, or 2; and each R$^{a1}$, R$^{b1}$, R$^{a2}$, R$^{b2}$, R$^{a3}$, R$^{b3}$, R$^{a4}$, and R$^{b4}$ is independently selected from F, CF$_3$, and H. In some embodiments, X is —COOH, —SO$_3$H, —OH, or —CF$_3$. In some embodiments, X is —COOH or —SO$_3$H.

In some embodiments, the composition further comprises a water-miscible organic solvent. In some embodiments, the water-miscible organic solvent is selected from dimethylsulfoxide, methanol, ethanol, N,N-dimethylformamide, and a polyethylene glycol.

In one aspect, disclosed herein is a composition comprising an environment-sensitive fluorophore, a protein, a polyfluoroalkyl substance, and an aqueous buffer solution.

In one aspect, disclosed herein is a use of differential scanning fluorimetry to determine a dissociation constant for a polyfluoroalkyl substance and a protein.

BRIEF DESCRIPTION OF THE DRAWINGS

In FIG. 4H, the regression of the change in temperature plotted against the logarithmic transformed concentration, in molar units, is also shown for GenX in DMSO and E1, along with chemical structures for GenX and E1.

DETAILED DESCRIPTION

Figure 1:
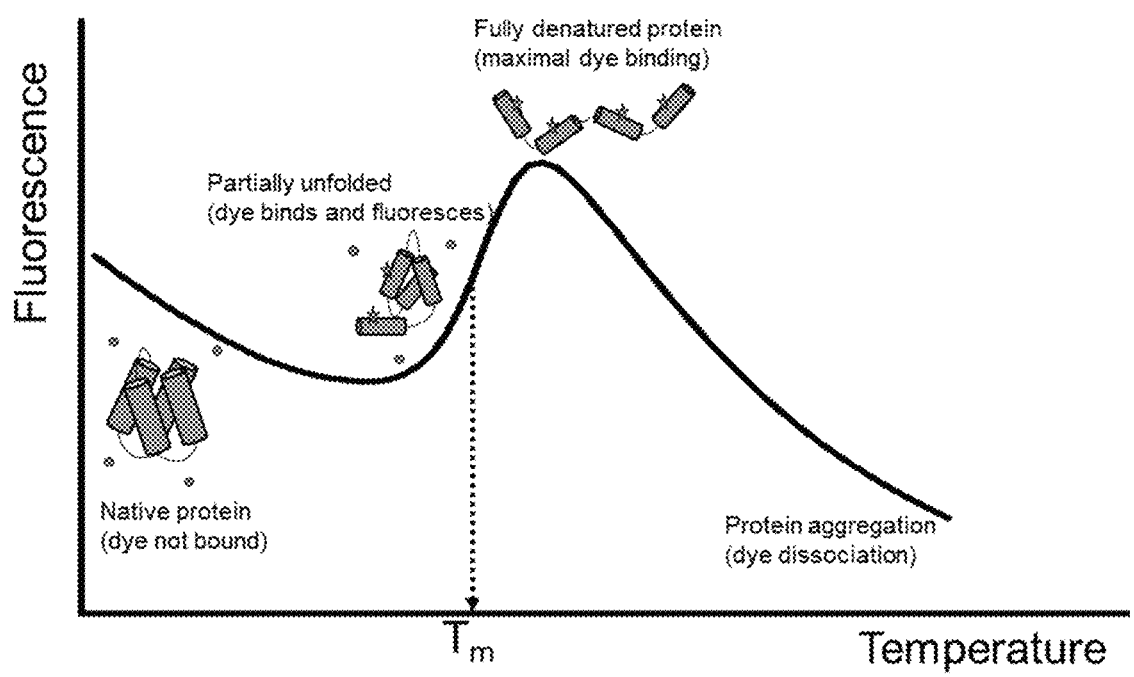
FIG. 1 shows an illustration of an environment-sensitive fluorophore can be used to monitor the temperature-dependent unfolding of a protein and determine the protein's melting temperature ($T_m$).

Disclosed herein are compositions and methods to rapidly characterize relative protein binding affinities of a variety of different PFAS. The methods can overcome limitations of standard technologies used to evaluate protein binding, including the facts that such approaches are time consuming, not scalable to high-throughput formats, require specialized instrumentation, and are often incompatible with the unique properties of many PFAS.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Sorrell, Organic Chemistry, 2$^{nd}$ edition, University Science Books, Sausalito, 2006; Smith, March's Advanced Organic Chemistry: Reactions, Mechanism, and Structure, 7$^{th}$ Edition, John Wiley & Sons, Inc., New York, 2013; Larock, Comprehensive Organic Transformations, 3$^{rd}$ Edition, John Wiley & Sons, Inc., New York, 2018; and Carruthers, Some Modern Methods of Organic Synthesis, 3$^{rd}$ Edition, Cambridge University Press, Cambridge, 1987; the entire contents of each of which are incorporated herein by reference.

The term "alkyl," as used herein, means a straight or branched saturated hydrocarbon chain. Alkyl groups can include from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "halogen" or "halo," as used herein, means F, Cl, Br, or I.

The term "haloalkyl," as used herein, means an alkyl group, as defined herein, in which one or more hydrogen atoms are replaced by a halogen. For example, one, two, three, four, five, six, seven or eight hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, and 2,2,2-trifluoroethyl.

The term "fluoroalkyl," as used herein, means an alkyl group, as defined herein, in which one or more hydrogen atoms are replaced by a fluorine. For example, one, two, three, four, five, six, seven eight, nine, ten, or more hydrogen atoms can be replaced by a fluorine. Representative examples of fluoroalkyl include, but are not limited to, fluoromethyl, difluoromethyl, trifluoromethyl, 2-fluoroethyl, 2,2-difluoroethyl, and 2,2,2-trifluoroethyl. The term "fluoroalkyl" encompasses the terms "polyfluoroalkyl" and "perfluoroalkyl," which are defined below.

The term "heteroalkyl," as used herein, refers "to an alkyl group, as defined herein, in which one or more of the carbon atoms (and any associated hydrogen atoms) are each independently replaced with a heteroatom group such as —NH—, —O—, —S—, —S(O)—, —S(O)$_2$—, and the like. By way of example, 1, 2, or 3 carbon atoms may be independently replaced with the same or different heteroatom group. Examples of heteroalkyl groups include, but are not limited to, —OCH$_3$, —CH$_2$OCH$_3$, —SCH$_3$, —CH$_2$SCH$_3$, —NHCH$_3$, and —CH$_2$NHCH$_3$. Heteroalkyl also includes groups in which a carbon atom of the alkyl is oxidized (i.e., is —C(O)—).

The term "polyfluoroalkyl," as used herein, means an alkyl group, as defined herein, in which two or more hydrogen atoms are replaced by a fluorine. For example, two, three, four, five, six, seven eight, nine, ten, or more hydrogen atoms can be replaced by a fluorine. Representative examples of polyfluoroalkyl include, but are not limited to, difluoromethyl, trifluoromethyl, 2,2-difluoroethyl, and 2,2,2-trifluoroethyl. The term "polyfluoroalkyl" encompasses the term "perfluoroalkyl," which is defined below.

The term "polyfluoroheteroalkyl," as used herein, means a heteroalkyl group, as defined herein, in which two or more hydrogen atoms are replaced by a fluorine. For example, two, three, four, five, six, seven eight, nine, ten, or more hydrogen atoms can be replaced by a fluorine. Representative examples of polyfluoroheteroalkyl include, but are not limited to, difluoromethoxy, trifluoromethoxy, and 2,2,2-trifluoroethoxy. The term "polyfluoroheteroalkyl" encompasses the term "perfluoroheteroalkyl," which is defined below.

The term "perfluoroalkyl," as used herein, refers to an alkyl group in which each hydrogen is replaced with fluorine. Representative examples of perfluoroalkyl include, but are not limited to, trifluoromethyl, perfluoroethyl, perfluoropropyl, perfluorobutyl, perfluoropentyl, and perfluorohexyl.

The term "perfluoroheteroalkyl," as used herein, means a heteroalkyl group, as defined herein, in which two or more hydrogen atoms are replaced by a fluorine. For example, two, three, four, five, six, seven eight, nine, ten, or more hydrogen atoms can be replaced by a fluorine. Representative examples of perfluoroheteroalkyl include, but are not limited to, trifluoromethoxy and 2,2,2-trifluoroethoxy. The term "polyfluoroheteroalkyl" encompasses the term "perfluoroheteroalkyl," which is defined below.

As used herein, the abbreviation "PFAS" refers to generally to poly- and perfluoroalkyl substances, which includes group shaving polyfluoroalkyl, perfluoroalkyl, polyfluoroheteroalkyl, and perfluoroheteroalkyl moieties.

Assay Methods and Compositions

Disclosed herein are thermal denaturation assays to evaluate changes in thermal stabilities of proteins in the presence of PFAS. The assays allow for rapid, high-throughput determination of protein binding properties for PFAS. More particularly, the methods disclosed herein involve determination of the difference in melting temperature ($T_m$) for the protein in the presence and the absence of the PFAS. When the $T_m$ for the protein is determined in compositions having different PFAS concentrations, the change in $T_m$ ($\Delta T_m$) can be used to determine dissociation constants ($K_d$) and $EC_{50}$ values. Also disclosed herein are compositions that can be used in the assays.

In particular, the methods disclosed herein comprise:
(a) providing a first composition comprising a polyfluoroalkyl substance, an environment-sensitive fluorophore, a protein, and an aqueous buffer solution, and determining a melting temperature ($T_m$) for the protein in the first composition;
(b) providing a second composition comprising the environment-sensitive fluorophore, the protein, and the aqueous buffer solution, and determining a melting temperature ($T_m$) for the protein in the second composition; and
(c) calculating the difference between the $T_m$ of the protein in the first composition and the $T_m$ of the protein in the second composition ($\Delta T_m$).

In some embodiments, the methods further comprise:
(d) providing N additional compositions, each of which comprises the environment-sensitive fluorophore, the protein, the polyfluoroalkyl substance, and the aqueous buffer solution, wherein N is at least 2, and determining a melting temperature ($T_m$) for the protein in each composition, wherein each additional composition comprises the polyfluoroalkyl substance at a different concentration; and
(e) for each of the N additional compositions, calculating the difference between the $T_m$ of the protein in the first composition and the $T_m$ of the protein in the additional composition ($\Delta T_m$).

In some embodiments, N is an integer selected from 2 to about 50, or from about 5 to about 20. For example, in some embodiments, N is 2, 3, 4, 5, 6, 7, 8, 9, 10, 11, 12, 13, 14, 15, 16, 17, 18, 19, or 20.

Compositions used in the methods disclosed herein include a PFAS. In some embodiments, the PFAS is a PFAS listed in the United States Environmental Protection Agency (EPA) Distributed Structure-Searchable Toxicity (DSSTox) database (accessible at https://comptox.epa.gov/dashboard/chemical_lists/PFASSTRUCT), the contents of which are incorporated herein by reference. In some embodiments, the PFAS is a PFAS listed in a report from the Organisation for Economic Co-operation and Development (OECD) entitled "Toward a New Comprehensive Global Database of Per- and Polyfluoroalkyl Substances (PFASs): Summary Report on Updating the OECD 2007 List of Per- and Polyfluoroalkyl Substances (PFASs)," OECD Environment, Health, and Safety Publications Series on Risk Management No. 39 (2018), which is incorporated herein by reference.

In some embodiments, the PFAS is a perfluoroalkylcarboxylic acid (PFCA), a perfluoroalkylsulfonic acid (PFSA), a fluorotelomer carboxylic acid, a fluorotelomer sulfonic acid, a fluorotelomer alcohol (FTOH), or a per- or polyfluoroalkyl ether acid (PFEA).

In some embodiments, the PFAS has a formula:

PFA-X wherein PFA is a polyfluoroalkyl group or a polyfluoroheteroalkyl group, and X is selected from the group consisting of —COOH, —SO$_3$H, —OH, —SO$_2$NH$_2$, —OC(O)CH=CH$_2$, —OC(O)C(CH$_3$)=CH$_2$, and —CF$_3$. In some embodiments, PFA is a C$_1$-C$_{12}$ polyfluoroalkyl group. In some embodiments, PFA is a C$_1$-C$_{12}$ perfluoroalkyl group. In some embodiments, PFA is a C$_1$-C$_{12}$ polyfluoroheteroalkyl group. In some embodiments, PFA is a C$_1$-C$_{12}$ perfluoroheteroalkyl group. In some embodiments, PFA has a formula —(CF$_2$)$_n$CF$_3$, wherein n is 1, 2, 3, 4, 5, 6, 7, 8, 9, 10, or 11 (e.g., wherein n is 2, 3, 4, 5, 6, 7, 8, 9, or 10). In some embodiments, PFA has a formula —(CH$_2$)$_2$(CF$_2$)$_n$CF$_3$, wherein n is 1, 2, 3, 4, 5, 6, 7, 8, or 9 (e.g., wherein n is 2, 3, 4, 5, 6, or 7). In some embodiments, PFA has a formula —(CR$^{a1}$R$^{b1}$)$_m$—O—(CR$^{a2}$R$^{b2}$CR$^{a3}$R$^{b4}$O)$_p$—(CR$^{a4}$R$^{B4}$)$_q$—CF$_3$, wherein: m is 1 or 2; p is 0, 1, or 2; q is 0, 1, or 2; and each R$^{a1}$R$^{b1}$, R$^{a2}$, R$^{b2}$, R$^{a3}$, R$^{b3}$, R$^{a4}$, $_{and}$R$^{b4}$ is independently selected from F, CF$_3$, and H. In some embodiments, X is —COOH. In some embodiments, X is —SO$_3$H. In some embodiments, X is —OH. In some embodiments, X is —CF$_3$.

In some embodiments, the PFAS is selected from the group consisting of perfluorobutanoic acid, perfluoropentanoic acid, perfluorohexanoic acid, perfluoroheptanoic acid, perfluorooctanoic acid (PFOA), perfluorononanoic acid (PFNA), perfluorodecanoic acid (PFDA), perfluoroundecanoic acid, perfluorododecanoic acid, perfluorotridecanoic acid, perfluorotetradecanoic acid, hexafluoropropylene oxide dimer acid, perfluorobutanesulfonic acid, perfluoropentanesulfonic acid, perfluorohexanesulfonic acid (PFHxS), perfluoroheptanesulfonic acid, perfluorooctanesulfonic acid (PFOS), perfluorononanesulfonic acid, perfluorodecanesulfonic acid, perfluorobutanesulfonamide, perfluoropentanesulfonamide, perfluorohexanesulfonamide, perfluoroheptanesulfonamide, perfluorooctanesulfonamide, perfluorobutanesulfonyl fluoride, perfluorooctanesulfonyl fluoride, 1H,1H,2H,2H-perfluorohexane-1-ol, perfluoro-3,6,9-trioxadecanoic acid, 7H-perfluoro-4-methyl-3,6-dioxaoctanesulfonic acid (Nafion byproduct 2), 1,1,1,2,2,3,3-heptafluoro-3-(1,2,2,2-tetrafluoroethoxy)propane, 1H,1H,2H,2H-perfluorooctanol, 2H,2H,3H,3H-perfluorohexanoic acid, 2H,2H,3H,3H-perfluorooctanoic acid, 2H,2H,3H,3H-perfluorononanoic acid, 2H,2H,3H,3H-perfluoroundecanoate, 2H,2H,3H,3H-perfluorohexansulfonic acid, and 2H,2H,3H,3H-perfluorooctane-1-sulfonate. In some embodiments, the PFAS is selected from the group consisting of perfluorobutanoic acid, perfluoropentanoic acid, perfluorohexanoic acid, perfluoroheptanoic acid, PFOA, PFNA, PFDA, perfluoroundecanoic acid, perfluorododecanoic acid, perfluorotetradecanoic acid, hexafluoropropylene oxide dimer acid, perfluorobutanesulfonic acid, PFHxS, PFOS, 1H,1H,2H,2H-perfluorohexane-1-ol, perfluoro-3,6,9-trioxadecanoic acid, 7H-perfluoro-4-methyl-3,6-dioxaoctanesulfonic acid (Nafion byproduct 2), 1,1,1,2,2,3,3-heptafluoro-3-(1,2,2,2-tetrafluoroethoxy)propane, 1H,1H,2H,2H-perfluorooctanol, 2H,2H,3H,3H-perfluorohexanoic acid, 2H,2H,3H,3H-perfluorooctanoic acid, 2H,2H,3H,3H-perfluorononanoic acid, 2H,2H,3H,3H-perfluoroundecanoate, 2H,2H,3H,3H-perfluorohexansulfonic acid, and 2H,2H,3H,3H-perfluorooctane-1-sulfonate.

The PFAS can be included in the composition at a variety of concentrations; in particular, in some embodiments, as described herein, a plurality of compositions can be prepared, each containing the PFAS of interest at a different concentration, ranging from about 0.001 mM to about 100 mM, or about 0.050 mM to about 10 mM. For example, in some embodiments, a composition (e.g., a composition that can be used in a method disclosed herein) includes a PFAS at a concentration of about 0.050 mM, 0.060 mM, 0.070 mM, 0.080 mM, 0.090 mM, 0.10 mM, 0.15 mM, 0.20 mM, 0.25 mM, 0.30 mM, 0.35 mM, 0.40 mM, 0.45 mM, 0.50 mM, 0.55 mM, 0.60 mM, 0.65 mM, 0.70 mM, 0.75 mM, 0.80 mM, 0.85 mM, 0.90 mM, 0.95 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, 3.5 mM, 3.6 mM, 3.7 mM, 3.8 mM, 3.9 mM, 4.0 mM, 4.1 mM, 4.2 mM, 4.3 mM, 4.4 mM, 4.5 mM, 4.6 mM, 4.7 mM, 4.8 mM, 4.9 mM, 5.0 mM, 5.1 mM, 5.2 mM, 5.3 mM, 5.4 mM, 5.5 mM, 5.6 mM, 5.7 mM, 5.8 mM, 5.9 mM, 6.0 mM, 6.1 mM, 6.2 mM, 6.3 mM, 6.4 mM, 6.5 mM, 6.6 mM, 6.7 mM, 6.8 mM, 6.9 mM, 7.0 mM, 7.1 mM, 7.2 mM, 7.3 mM, 7.4 mM, 7.5 mM, 7.6 mM, 7.7 mM, 7.8 mM, 7.9 mM, 8.0 mM, 8.1 mM, 8.2 mM, 8.3 mM, 8.4 mM, 8.5 mM, 8.6 mM, 8.7 mM, 8.8 mM, 8.9 mM, 9.0 mM, 9.1 mM, 9.2 mM, 9.3 mM, 9.4 mM, 9.5 mM, 9.6 mM, 9.7 mM, 9.8 mM, 9.9 mM, or 10 mM, or any range therebetween.

Compositions used in the methods disclosed herein also include an environment-sensitive fluorophore. Environment-sensitive fluorophores are a class of chromophores that have spectroscopic behavior that is dependent on the physicochemical properties of the surrounding environment. For example, environment-sensitive fluorophores may display sensitivity to the physicochemical properties of the surrounding environment (e.g., polarity), or may become fluorescent only if rotation is constrained (e.g., when the viscosity of the environment changes). The latter are referred to as fluorescent molecular rotors. Environment-sensitive fluorophores may exhibit low quantum yields in aqueous solution, but become highly fluorescent in nonpolar solvents or when bound to hydrophobic sites in proteins.

Examples of environment-sensitive fluorophores include, but are not limited to, 2-propionyl-6-dimethylaminonaphthalene (PRODAN), 4-dimethylamino phthalimide (4-DMAP), 4-amino-1,8-naphthalimide derivatives (e.g., 4-N,N-dimethylamino-1,8-naphthalimide (4DMN)), nitrobenzoxadiazole fluorophores (e.g., 7-nitrobenz-2-oxa-1,3-diazole (NBD)), 9-(2-carboxy-2-cyanovinyl)julolidine (CCVJ), 9-(2,2-dicyanovinyl)julolidine (DCVJ), 4-(4-(dimethylamino)styryl)-N-methylpyridinium iodide, and GloMelt™ dye (Biotium, Hayward, CA). In some embodiments, the environment-sensitive fluorophore is selected from 9-(2-carboxy-2-cyanovinyl)julolidine (CCVJ), 9-(2,2-dicyanovinyl)julolidine (DCVJ), 4-(4-(dimethylamino)styryl)-N-methylpyridinium iodide, and GloMelt™ dye (Biotium, Hayward, CA). In some embodiments, the environment-sensitive fluorophore is GloMelt™ dye. Certain dyes will not be compatible with the assays, particularly when amphipathic PFAS are used, because they are not compatible with assays containing detergents. Examples of environment-sensitive fluorophores that are not compatible with an assay containing a surfactant or detergent are SYPRO Orange and Proteostat TS.

The environment-sensitive fluorophore can be included in the compositions at a variety of concentrations. For example, in some embodiments, the environment-sensitive fluorophore is included in the composition in an amount of about 0.05 mg/mL to about 1.0 mg/mL, e.g., about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or about 1.0 mg/mL, or any range therebetween. One skilled in the art will understand that the optimal concentration of the environment-sensitive fluorophore, to maximize signal-to-noise ratio in the assay, can be readily determined with routine experimentation.

Compositions used in the methods disclosed herein also include a protein. The protein can be any protein for which the potential of PFAS binding is of interest, including full-length proteins or specific protein domains. Proteins can be obtained from commercial sources, or can be prepared using standard protein expression techniques. One skilled in the art will appreciate that in order to determine binding affinities for PFAS compounds to proteins, the assay should be conducted under conditions in which proper protein structure is maintained. This can be achieved, for example, by using appropriate buffer systems.

In some embodiments, the protein is an albumin protein. In some embodiments, the protein is selected from human serum albumin, bovine serum albumin, porcine serum albumin, rat serum albumin, and rabbit serum albumin. For example, human serum albumin (HSA) is the primary blood protein responsible for distribution of hormones, nutrients, drugs, and many toxicants. Many PFAS are known to bind to HSA; it is the primary transport protein for PFOS, PFOA, PFNA, PFHxS, and PFDA. It contains multiple non-specific binding sites that selectively bind fatty acids, hormones, drugs, and some xenobiotics including PFAS (Forsthuber et al. Environ. Int. 137, 105324 (2020)). Albumin proteins are known to be glycated; for example, glycated albumin is a marker for disease states such as diabetes. Both glycated and un-glycated albumin can be used in the methods disclosed herein.

In addition to albumin proteins, other proteins that can be used in the methods disclosed herein include fatty acid binding proteins, immunoglobulins, peroxisome proliferator-activated receptors, and thyroid proteins (e.g., thyroglobulin).

Fatty acid binding proteins (FABPs) are a group of molecules that coordinate lipid responses in cells and are also strongly linked to metabolic and inflammatory pathways. They are abundantly-expressed proteins that reversibly bind hydrophobic ligands, such as saturated and unsaturated long-chain fatty acids, eicosanoids and other lipids, with high affinities. FABPs are found across numerous species, including humans.

Immunoglobulins (also known as antibodies) are proteins that are present in the serum and cells of the immune system. Particular classes of antibodies include immunoglobulin A (IgA), immunoglobulin D (IgD), immunoglobulin E (IgE), immunoglobulin G (IgG), and immunoglobulin M (IgM). In some embodiments, the protein is immunoglobulin G.

Peroxisome proliferator-activated receptors (PPARs) are nuclear receptor proteins that function as transcription factors, regulating the expression of genes. Three types of PPARs have been identified, which are differentially expressed in various tissues: PPAR-α(liver, kidney, heart, muscle, adipose tissue, and others); PPAR-β/δ (many tissues including brain, adipose tissue, and skin; and PPAR-γ (most tissues, with three forms produced through alternative splicing—PPAR-γ1, PPAR-γ2, and PPAR-γ3. In some embodiments, the protein is PPAR-α or PPAR-γ.

Proteins produced by the thyroid gland include thyroglobulin, thyroid peroxidase, and iodotyrosine deiodinase. In particular, thyroglobulin is a substrate for the synthesis of the thyroid hormones thyroxine (T4) and triiodothyronine (T3). PFAS have been shown to cause abnormal levels of thyroid hormones, and PFAS are known to bind to thyroglobulin (Ren et al. Toxicology 366-367, 34-24 (2016)). Accordingly, in some embodiments, the protein is thyroglobulin.

The protein can be included in the composition in an amount of about 0.01 mM to about 1.0 mM, or about 0.05 mM to about 0.75 mM. For example, the protein can be included in the composition in an amount of about 0.01, 0.02, 0.03, 0.04, 0.05, 0.06, 0.07, 0.08, 0.09, 0.10, 0.125, 0.15, 0.175, 0.20, 0.225, 0.25, 0.275, 0.30, 0.325, 0.35, 0.375, 0.40, 0.425, 0.45, 0.475, 0.50, 0.525, 0.55, 0.575, 0.60, 0.625, 0.65, 0.675, 0.70, 0.725, 0.75, 0.775, 0.80, 0.825, 0.85, 0.875, 0.90, 0.925, 0.95, 0.975, or 1.0 mM. One skilled in the art will understand that the optimal protein concentration, to maximize signal-to-noise ratio in the assay, can be readily determined with routine experimentation.

Compositions used in the methods disclosed herein further comprise an aqueous buffer solution. Use of a buffer to control the pH of the solution is important in certain embodiments, such as when the PFAS is a polyfluorinated carboxylic acid or a polyfluorinated sulfonic acid. In some embodiments, the aqueous buffer solution can comprise any buffer components that maintain a pH of about 7.0 to about 7.5 (e.g., about 7.2 to about 7.4) across a range of temperatures such as those used in assays to determine protein melting temperature. In some embodiments, the aqueous buffer solution comprises 4-(2-hydroxyethyl)-1-piperazineethanesulfonic acid (HEPES). In some embodiments, the aqueous buffer solution comprises a salt, such as sodium chloride. In some embodiments, the aqueous buffer solution is HEPES-buffered saline.

Compositions used in the methods disclosed herein can optionally comprise additional components. For example, in some embodiments, the compositions further comprise a water-miscible organic solvent, such as dimethylsulfoxide, methanol, ethanol, NN-dimethylformamide, or a polyethylene glycol, or a mixture of any thereof. The water-miscible organic solvent can be used to solubilize a PFAS compound that has limited solubility in aqueous solution. In some embodiments, the composition further comprises dimethylsulfoxide in an amount of up to about 50% of the final volume of the composition (e.g., up to 5 vol %, up to 10 vol %, up to 15 vol %, up to 20 vol %, up to 25 vol %, up to 30 vol %, up to 35 vol %, up to 40 vol %, up to 45 vol %, or up to 50 vol %). In some embodiments, the composition further comprises methanol in an amount of up to about 30% of the final volume of the composition (e.g., up to up to 5 vol %, up to 10 vol %, up to 15 vol %, up to 20 vol %, up to 25 vol %, or up to 30 vol %).

In some embodiments, the compositions further comprise a passive reporter dye, such as carboxyrhodamine. Use of a passive reporter dye is optional but can improve replicate consistency in assays disclosed herein, e.g., by normalizing the fluorescent signal and reducing variability between technical replicates. A passive reference signal can also be used to correct for issues such as formation of bubbles in a sample, to detect pipetting errors or poor mixing, evaporation losses, and the like.

The methods disclosed herein involve determining the melting temperature ($T_m$) for the protein in the compositions (e.g., the first and second compositions disclosed above). In some embodiments, the $T_m$ is determined using differential scanning fluorimetry (DSF). The use of DSF for determining $T_m$ values (and ultimately $K_d$ and $EC_{50}$ values, as described further below) has advantages over typical methods, including titration chemistry or surface plasmon resonance, which are resource-intensive and time-consuming. For example, DSF requires substantially lower amounts of protein, and the assay can be completed in only a few hours. Additionally, DSF is performed using real-time PCR instruments that are widely available and accessible by most laboratories.

In the DSF method, the temperature of each composition (e.g., the first composition, the second composition, and optionally the N additional compositions as discussed above) is slowly increased. The initial background fluorescence is generally low, as the environment-sensitive fluorophore in each composition is free in solution. However, as the temperature of the solution is increased, the protein begins to unfold which provides more sites for the fluorophore to bind, causing an increase in fluorescence. As the temperature continues to increase, the protein will fully denature and maximal fluorophore binding will occur. After this point, as heating continues, protein aggregation will begin to occur, and fluorescence will rapidly decline as the fluorophore dissociates from the protein. This is illustrated generally in FIG. 1. The point at which ~50% of the protein is in an unfolded state is the melting temperature ($T_m$) of the protein.

The DSF method generally involves increasing the temperature at a given ramp rate (e.g., 0.2° C./sec), over a temperature range of about 37° C. to about 99° C. The first derivative of the fluorescence data (df/dt) can be calculated for each cycle (e.g., (Fluorescence Cycle 2—Fluorescence Cycle 1)/$\Delta T$), and the peak of the resulting first derivative curve, indicating the maximum slope of the increasing fluorescence as protein unfolds, indicates the protein is in equilibrium between folded and unfolded states—this is deemed the $T_m$.

In compositions that include the PFAS, if the protein binds the compound, the protein may be stabilized (or in some cases, destabilized). This stabilization effect is indicated by an increase in the melting temperature of the protein ($\Delta T_m$). As the concentration of PFAS continues to increase, the melting temperature will generally further increase until it reaches a maximum stabilizing effect.

In some embodiments, the methods further comprise the step of plotting the $\Delta T_m$ for each composition against the concentration of the polyfluoroalkyl substance, and fitting the data to the following equation:

$$Y = \text{Bottom} + \frac{(\text{Top} - \text{Bottom}) * \left(1 - \left(P - Kd - X + \sqrt{(P + X + Kd)^2 - (4*P*X)}\right)\right)}{2*P}$$

wherein:
Top is maximal response (i.e. the maximum $\Delta T_m$);
Bottom is minimal response (i.e. the minimum $\Delta T_m$);
P is protein concentration;
$K_d$ is dissociation constant;
X is polyfluoroalkyl substance concentration; and
Y is $\Delta T_m$;
to thereby determine the dissociation constant for the polyfluoroalkyl substance and the protein.

In some embodiments, the methods further comprise the step of plotting the $\Delta T_m$ for each composition against the log-transformed PFAS concentration (log[PFAS]) and fitting the data to the following standard four-parameter curve:

$$Y = \text{Bottom} + \frac{(\text{Top} - \text{Bottom})}{1 + 10^{\wedge}((\text{Log}EC50 - X)*HillSlope)}$$

wherein:

Top is maximal response;

Bottom is minimal response;

Log $EC_{50}$ is the log-transformed half-maximal effective concentration;

X is ligand concentration;

HillSlope is the Hill coefficient; and

Y is $\Delta T_m$.

The Hill coefficient indicates cooperativity of binding—a Hill coefficient of 1 indicates independent binding, >1 indicates positive cooperativity, and <1 indicates negative cooperativity.

The methods disclosed herein can be conducted with each composition in a separate well of a multi-well plate, such as a 96-well plate or a 384-well plate. This allows high-throughput screening of multiple concentrations of multiple PFAS in a single plate.

As demonstrated in the Examples section, the methods disclosed herein were validated by determining the binding affinities for natural albumin ligands, namely octanoic acid, decanoic acid, hexadecanoic acid, ibuprofen, and warfarin. The binding affinities for these compounds determined using the methods disclosed herein matched the known binding affinities that have been reported.

The following examples further illustrate aspects of the disclosure but, of course, should not be construed as in any way limiting its scope.

EXAMPLES

Materials and Methods

Figure 2:
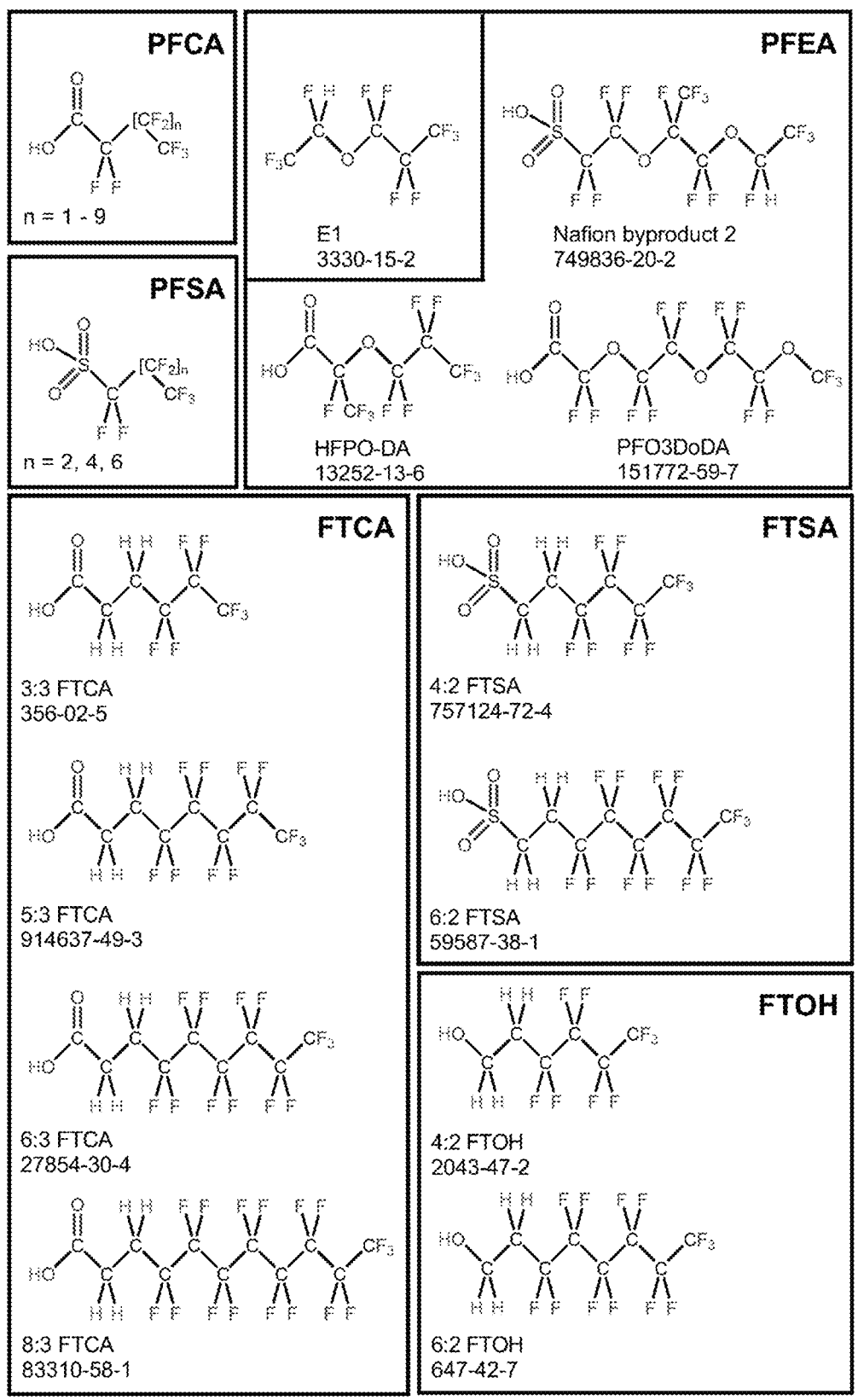
FIG. 2 shows structures of PFAS used in methods disclosed herein.

Reagents and solvents used were the highest purity available. All aqueous buffers and solutions were prepared in sterile Milli-Q A10 water (18Ω; 3 ppb total oxidizable organics). GloMelt (λEx=468 nm λEm=507 nm) and carboxyrhodamine (ROX; λEx=588 nm λEm=608 nm) dyes were purchased from Biotium (Fremont, CA). Structures of PFAS analyzed are shown in FIG. 2. Octanoic acid (CAS 124-07-2, purity≥98%), Perfluorobutanoic acid (PFBA, CAS 375-22-4, purity≥99%), perfluoropentanoic acid (PFPeA, CAS 2706-90-3, purity≥97%), perfluoroheptanoic acid (PFHpA, (CAS 375-85-9, purity≥98%), PFOA (CAS 335-67-1 purity≥95%), perfluorodecanoic acid (PFDA, CAS 335-76-2, purity≥97%), perfluorododecanoic acid (PFDoA, CAS 307-55-1, purity≥96%), perfluorotetradecanoic acid (PFTDA, CAS 376-06-7, purity≥96%), and HFPO-DA (CAS 13252-13-6, purity≥97%) were from Alfa Aesar (Havermill, MA). Perfluorohexanoic acid (PFHxA, CAS 307-24-4, purity≥98%), perfluorononanoic acid (PFNA, CAS 375-95-1, purity≥95%), Perfluorobutanesulfonic acid (PFBS, CAS 375-73-5, purity≥98%), Warfarin (CAS 81-81-2, purity≥98%), and 1H,1H,2H,2H-Perfluorohexane-1-ol (4:2-FTOH, CAS 2043-47-2, purity≥97%) were from TCI America (Portland, OR). Perfluoroundecanoic acid (PFunDA, CAS 2058-94-8, purity≥96%) was from Oakwood Chemical (Estill, S. C.), perfluorohexanesulfonic acid (PFHxS, CAS 3871-99-6, purity≥98%) was from J&K Scientific (Beijing, China), and PFOS (CAS 2795-39-3, purity≥98%) and Perfluoro-3,6,9-trioxadecanoic acid (PFO3DoDA, CAS 151772-59-7, purity 98%) were from Matrix Scientific (Columbia, S. C.). Nafion byproduct 2 (CAS 749836-20-2, purity≥95%), 1,1,1,2,2,3,3-Heptafluoro-3-(1,2,2,2-tetrafluoroethoxy)propane (E1, CAS 3331-15-2, purity≥97%), 1H,1H,2H,2H-Perfluorooctanol (6:2-FTOH, CAS 647-42-7, purity≥97%), 2H,2H,3H,3H-Perfluorohexanoic acid (3:3-FTCA, CAS 356-02-5, purity≥97%), 2H,2H,3H,3H-Perfluorooctanoic acid (5:3-FTCA, CAS 914637-49-3, purity≥97%), 2,H,2H,3H,3H-Perfluorononanoic acid (6:3-FTCA, CAS 27854-30-4, purity≥97%), 2,H,2H,3H,3H-Perfluoroundecanoate (8:3-FTCA, CAS 83310-58-1, purity≥97%), 2H,2H,3H,3H-Perfluorohexansulfonic acid (4:2-FTSA, CAS 757124-72-4, purity≥97%) and 2H,2H,3H,3H-Perfluorooctane-1-sulfonate (6:2 FTSA, CAS 59587-39-2, purity≥97%) were from Synquest Laboratories (Alachua, FL). HSA (CAS 70024-90-7, purity≥95%, fraction V fatty acid free) and hexadecanoic acid (CAS 57-10-3, natural, purity≥98%) were from Millipore Sigma (Burlington, MA). Porcine serum albumin (PSA), bovine serum albumin (BSA), and rat serum albumin (RSA), were from Sigma-Aldrich. HEPES (4-(2-hydroxyethyl)-1-piperazineethanesulfonic acid), sodium chloride, methanol, dimethylsulfoxide, decanoic acid (CAS 334-48-5, purity≥99%) and ibuprofen (CAS 15687-27-1, purity≥99%), and potassium chloride (KCl, CAS 7447-40-7, purity≥99.7%) were purchased from Thermo Fisher (Waltham, MA).

Stock solutions (20 mM) of PFBA, PFPeA, PFHxA, PFHpA, PFOA, PFBS, PFHxS, PFOS, HFPO-DA, Nafion bp2, 6:3-FTCA, 6:2-FTSA, decanoic acid, ibuprofen, and KCl were prepared in aqueous 1x HEPES buffered saline (HBS, 140 mM NaCl, 50 mM HEPES, 0.38 mM $Na_2HPO_4$, pH 7.2). A 1:1 mixture of HBS and DMSO was used as a solvent for PFNA, PFDA, PFunDA, and 8:3-FTCA stocks, and the fatty acids and warfarin were dissolved into FIBS supplemented with 30% methanol. For experiments evaluating possible solvent effects, 20 mM stock solutions of PFOA were prepared in all three solvents. The FIBS concentrations used in solvents containing DMSO or methanol were adjusted to ensure that the final concentration of the thermal denaturation buffer contained 140 mM NaCl, 50 mM HEPES, 0.38 mM $Na_2HPO_4$. Solution pH for PFAS stocks were confirmed to be 7.4 and stocks were stored at −20° C. For thermal stability concentration response analysis stock solutions were serially diluted into solvent. Stocks of HSA (or PSA, BSA, or RSA) (1 mM) were prepared in 2× HBS and then diluted with an equal volume of $H_2O$ to final desired concentrations.

Example 1: Measurement of HSA Binding Affinities

Temperature control and fluorescence detection were performed using a Step One Plus Real-Time PCR System (Applied Biosystems; Grand Island, NY) with indicator dye (GloMelt) fluorescence (λEx=468 nm λEm=507 nm) detected using the FAM/SYBR filter set and the passive reference dye carboxyrhodamine (λEx=588 nm λEm=608 nm) detected using the ROX channel. Thermal denaturation was performed in sealed optical 96-well reaction plates (MicroAmp Fast, Applied Biosystems) using the following conditions: 10 minutes at 37° C. for one holding stage, followed by a ramp profile from 37° C. to 99° C. at a rate of 0.2° C./sec. Assays were also performed in 384-well plates, in which the reactions were performed using half the final volume (10 μL) and the concentration of each reagent was halved compared to those used in the 96-well plates. Following optimization, each differential scanning fluorimetry (DSF) assay contained 0.125 mM HSA in a final volume of 20 μl. Stock solutions of each test chemical were serially diluted into HBS, with final concentrations ranging from 50 μM to 10 mM. Working fluorophore solutions (200× in 0.1% DMSO) diluted 1:20, and ROX (40 μM) diluted 1:10 were prepared immediately prior to each experiment with 2 μl of each used for each assay. At least two independent plates were run for each experimental unit. Controls run on each plate included matching vehicle control (no ligand; KCl added for potassium salts), no protein control, and a minimum of three concentrations of decanoic acid as a positive control for protein stabilization. To evaluate the sensitivity of the assay to detect DMSO mediated conversion of HPFO-DA to E1 (Liberatore et al. Environ. Sci. Technol. Lett. 7, 477-481 (2020)), HFPO-DA was prepared in a 1:1 mixture of HBS and DMSO and maintained at room temperature for 4 hours before experimental analysis.

All presented DSF data are representative of multiple experiments each containing 3 replicates for each sample. Matching vehicle blank controls lacking test compound were included on the same plate for each experiment. Raw thermocycler data were exported to Excel (Microsoft) and statistical analysis was performed using SPSS v26 (IBM, Armonk, NY) or GraphPad Prism (v8.3.0, GraphPad Software Inc., San Diego, CA). Data are reported as mean values±SEM following background subtraction. Assay data is reported in relative fluorescent light units (RFU). The $T_m$ is defined as the temperature at which the maximum change in fluorescence is observed, indicating half of the protein is unfolded. PFAS concentration response curves were smoothed using the Savitzky and Golay method (Savitzky et al. Anal. Chem. 36, 1627-1639 (1964)), $EC_{50}$ estimates are derived using a 4-parameter variable slope model, and dissociation constants were calculated using a single site ligand binding model using the formula (Vivoli et al. J. Vis. Exp. (2014) doi:10.3791/51809):

$$Y = \text{Bottom} + \frac{(\text{Top} - \text{Bottom}) * \left(1 - \left(P - Kd - X + \sqrt{(P + X + Kd)^2 - (4*P*X)}\right)\right)}{2*P}$$

Top is the maximal response, bottom is minimal response, P is protein concentration, $K_d$ is dissociation constant, X is ligand concentration, and Y is change in $T_m$. The relationship between number of aliphatic carbons or number of fluorine and the binding affinity of HSA for each compound was determined using a second order polynomial (quadratic) best fit with least squares regression. Comparison between protein concentrations and comparisons of calculated binding affinities between different compounds was performed using one-way analysis of variance (ANOVA) and a Tukey's post hoc test was performed to evaluate pair-wise differences. Significance between differences in values was defined as p<0.05.

Figures 3A, 3B, 3C, 3D, 3E, 3F:
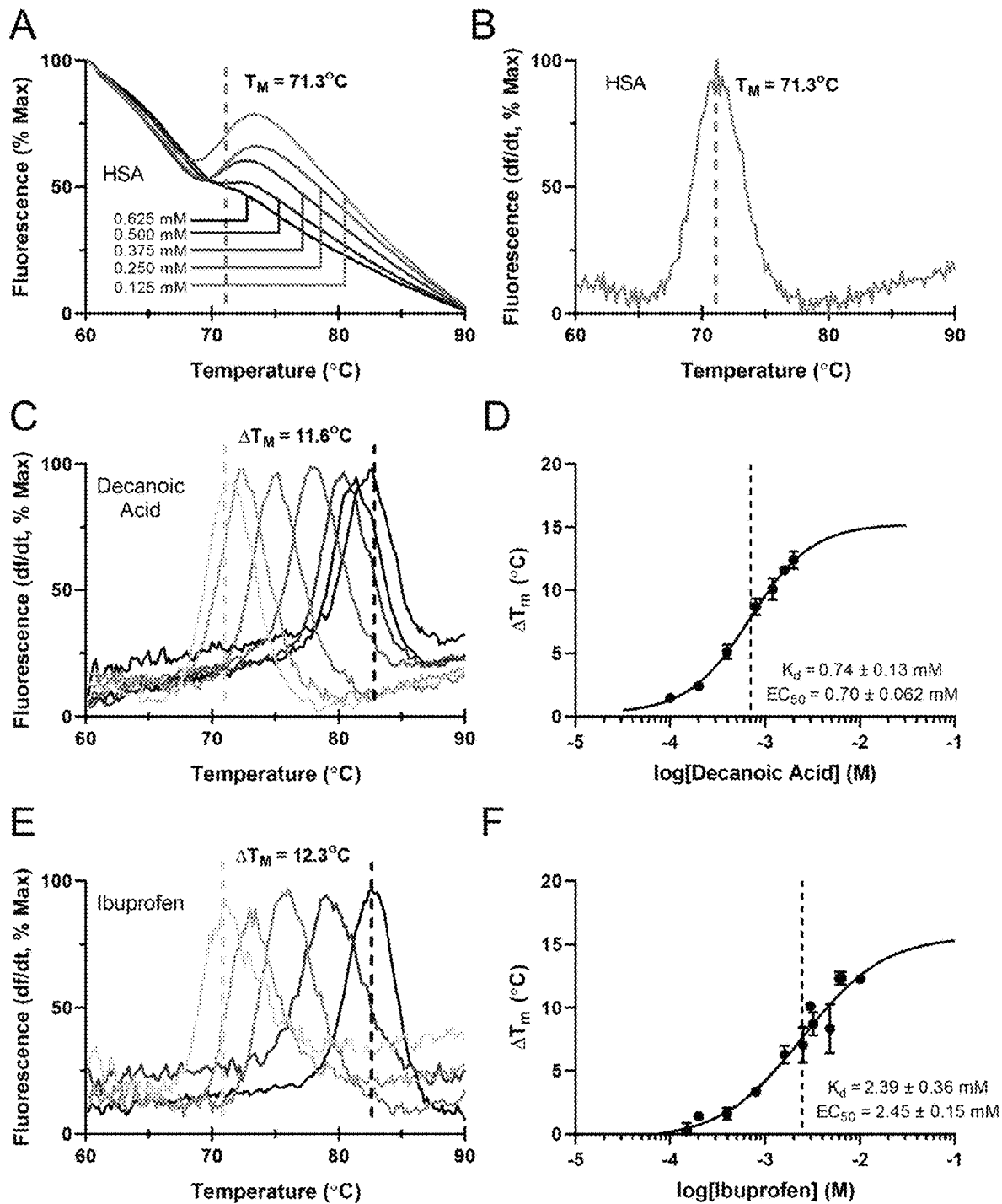
FIGS. 3A-3F show data validating the differential scanning fluorimetry method for measuring control compound binding. The fluorescence of HSA alone, normalized to the % maximum, as temperature was increased from 60-90° C. is shown with the melting temperature indicated as the point at which half of the protein is inferred to be unfolded (FIG. 3A). Increasing concentrations of HSA (0.125 mM to 0.625 mM) from light gray to black are shown. The derivative fluorescence of HSA alone, plotted as the derivative of fluorescence divided by the derivative of time, as temperature was increased from 60-90° C. is shown with the melting temperature indicated as the maximum of the derivative curve (FIG. 3B). Derivative fluorescent curves for HSA with the fatty acid decanoic acid (FIG. 3C) or known albumin binding compound ibuprofen (FIG. 3E) as temperature was increased from 60-90° C., are shown with increasing concentrations of compound indicated by increasing wavelength of color from violet to red. The maximum change in temperature for HSA alone is shown between the dashed gray and red lines. The regression of the change in temperature plotted against the logarithmic transformed concentration, in molar units, is shown for decanoic acid (FIG. 3D) and ibuprofen (FIG. 3F), with the log($EC_{50}$) indicated by a dashed line. n≥3 across at least two replicate plates for all compounds.

For thermal melt assay optimization, concentrations of HSA between 0.05 mM to 0.625 mM were evaluated to identify the HSA concentration that yielded maximal signal to noise ratio (FIG. 3A). The observed $T_m$ for HSA (71.3° C.) did not vary across the concentration range analyzed (F (4, 10)=2.19, p=0.14; FIG. 3B). Optimal performance was for assays containing 0.125 mM HSA (FIG. 3A). Including an initial 10-minute preincubation at 37° C. decreased the relatively high initial fluorescence observed for HSA, and the optimal temperature ramp rate was determined to be 0.2° C./sec. Most compounds were sufficiently soluble to use 1x HBS as a solvent for 20 mM stock solutions. The limited aqueous solubility of the C9-C11 PFCA and 8:3-FTCA required use of HBS containing 50% DMSO, and the fatty acids and warfarin required using 30% methanol as a solvent. Possible solvent effects were investigated for PFOA that was solubilized in each of the three solvents. Assay results for HSA binding of PFOA binding were not significantly influenced by the stock solution solvent (F (2, 15)=0.005, p=0.996) (Table 1). The increase in potassium ions from the potassium salts of PFHxS, PFOS, 8:3-FTCA, and 6:2-FTSA did not affect assay results (data not shown).

TABLE 1

Analysis of Solvent Effects
Table 1. Analysis of solvent effects

| Solvent | Kd (mM) | EC50 (mM) | Δ Tm (° C.) |
|---|---|---|---|
| HEPES-buffered saline (HBS) | 0.83 ± 0.11 | 0.84 ± 0.04 | 13.5 |
| Methanol (30% in HBS) | 0.83 ± 0.06 | 0.78 ± 0.07 | 13.5 |
| DMSO (50% in HBS) | 0.84 ± 0.08 | 0.85 ± 0.01 | 13.2 |

Δ Tm is ° C., EC50 and $K_d$ are mean values reported in ± SEM. Each compound was run on at least two separate plates with n ≥ 4

Measurement of HSA binding affinity for known HSA binding compounds Octanoic acid, decanoic acid, hexadecenoic acid, warfarin, and ibuprofen were used as positive controls to evaluate whether DSF estimates of binding affinities were comparable to published values using other methods. Analysis of the fatty acid-induced melting temperature shift of HSA determined a $K_d$ of 2.10±0.19 mM for octanoic acid, 0.74±0.13 mM for decanoic (FIGS. 3C and 3D), and 0.030±0.008 for hexadecanoic acid (Table 2). Two-way ANOVA revealed that the fatty acids were significantly different (F (2, 15)=63, p<0.0001), with Tukey's post-hoc comparison indicating that each fatty acid was significantly different from the other two examined. The calculated $K_d$ for HSA binding of ibuprofen was 2.39±0.36 mM (FIGS. 3E-3F) and warfarin was 0.16±0.041 mM (Table 2). The calculated affinities of HSA binding for each of all compounds are within the range of previously determined values (Beesoon et al. Environ. Sci. Technol. 49, 5722-5731 (2015); Takehara et al. Anal. Sci. Int. J. Jpn. Soc. Anal. Chem. 25, 115-120 (2009); Spector, J. Lipid Res. 16, 165-179 (1975); Lee et al. J. Biol. Chem. 255, 6121-6127 (1980)).

TABLE 2

Binding affinity of HSA for control compounds

| Compounds | CAS ID | $R^2$ | Δ Tm (° C.) | EC50 (mM) | $K_d$ (mM) |
|---|---|---|---|---|---|
| Octanoic Acid | 124-07-2 | 0.93 | 3.1 ± 0.10 | 2.15 ± 0.10 | 2.10 ± 0.19 |
| Decanoic Acid | 334-48-5 | 0.98 | 12.4 ± 0.29 | 0.70 ± 0.062 | 0.74 ± 0.13 |
| Hexadecanoic Acid | 57-10-3 | 0.95 | 7.2 ± 0.073 | 0.084 ± 0.021 | 0.03 ± 0.008 |
| Ibuprofen | 15687-27-1 | 0.97 | 12.3 ± 0.14 | 2.45 ± 0.15 | 2.39 ± 0.36 |
| Warfarin | 81-81-2 | 0.97 | 9.3 ± 0.12 | 0.19 ± 0.023 | 0.16 ± .041 |

Δ Tm is ° C., $EC_{50}$ and $K_d$ are mean values reported in ± SEM. Each compound was run on at least two separate plates with n ≥ 4

Measurement of Albumin Binding Affinity for PFAS

Figures 4A, 4B, 4C, 4D, 4E, 4F, 4G, 4H:
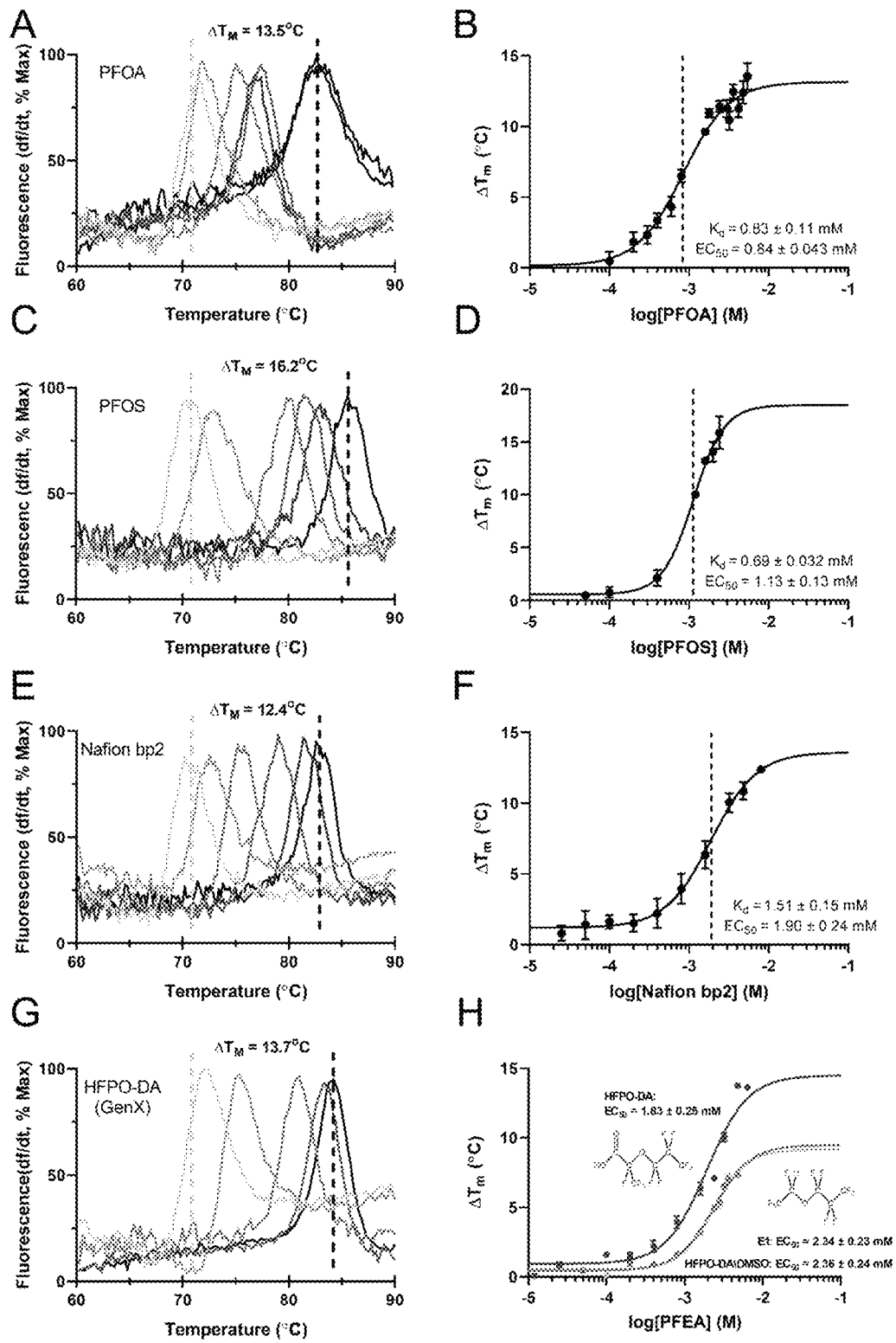
FIGS. 4A-4H show data validating the differential scanning fluorimetry method for measuring PFAS binding. Derivative fluorescent curves for HSA with the PFAA PFOA (FIG. 4A), PFOS (FIG. 4C), and Nafion byproduct 2 (FIG. 4E), HFPO-DA (GenX) (FIG. 4G), as temperature was increased from 60-90° C., are shown with increasing concentrations of compound indicated by increasing wavelength of color from violet to red. The maximum change in temperature from HSA alone is shown between the dashed gray and red lines. The regression of the change in temperature plotted against the logarithmic transformed concentration, in molar units, is shown for PFOA (FIG. 4B), PFOS (FIG. 4D), Nafion byproduct 2 (FIG. 4F), and GenX (FIG. 4H) with the log($EC_{50}$) indicated by a dashed line. n≥3 across at least two replicate plates for all compounds.
Figures 5A, 5B, 5C, 5D:
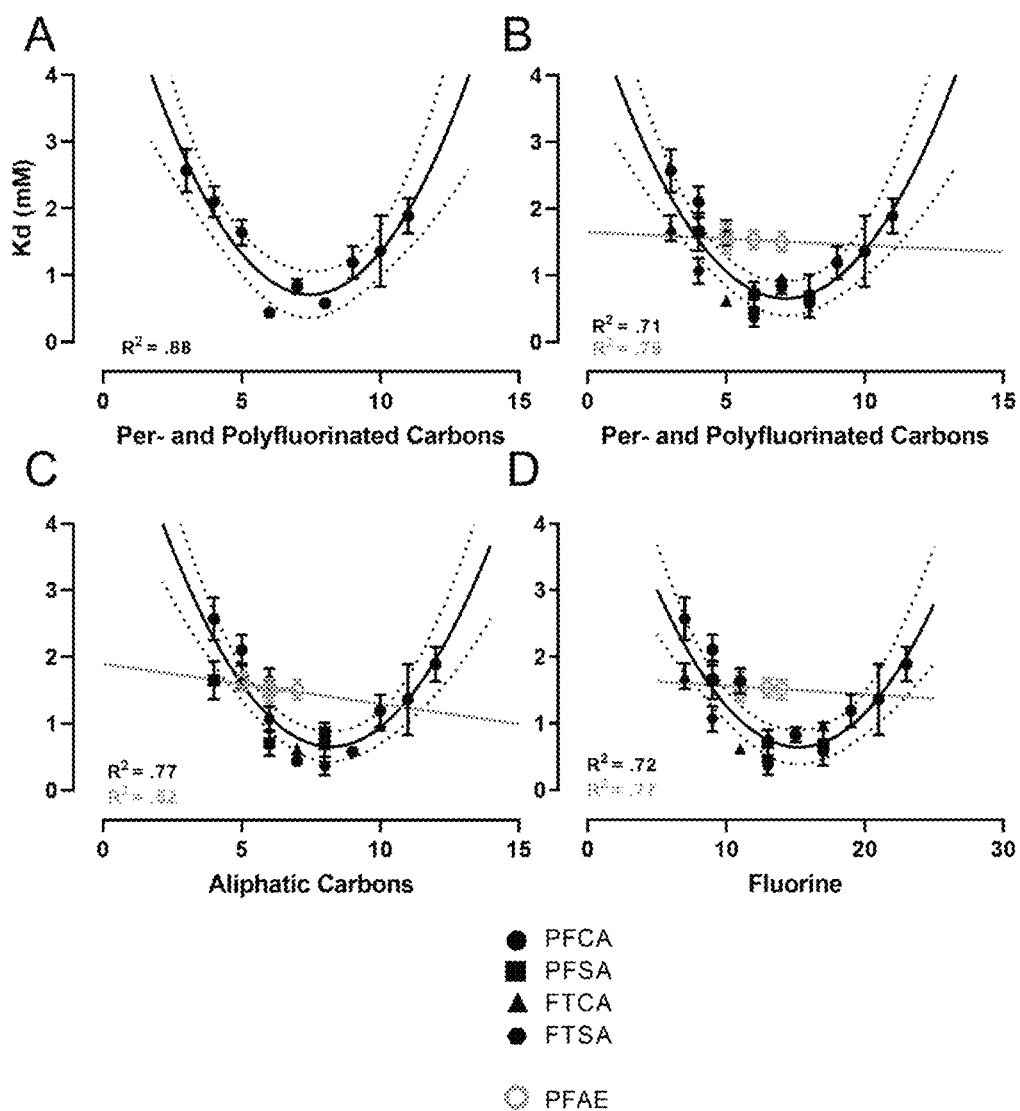
FIGS. 5A-5D show data for the effect of carbon chain length and fluorine moieties on PFAS binding. The binding affinity of the PFCA (FIG. 5A) and all analyzed PFAAs and PFAEs (FIGS. 5B-D) are plotted against the number of per- and polyfluorinated carbons (FIGS. 5A-B), aliphatic carbons, (FIG. 5C), or fluorine (FIG. 5D). For all PFAAs except PFAE, a quadratic line of best fit with 95% confidence interval in dashed lines was generated using least squares regression.

Numerous studies have evaluated albumin binding of PFOA and PFOS (Hebert et al. *Anal. Chem.* 82, 6463-6471 (2010); Chen et al. Arch. Toxicol. 83, 255-261 (2009); Sabin et al. *Biomacromolecules* 7, 176-182 (2006); Han et al. *Chem. Res. Toxicol.* 16, 775-781 (2003); Bischel et al. *Environ. Sci. Technol.* 44, 5263-5269 (2010); Beesoon et al. *Environ. Sci. Technol.* 49, 5722-5731 (2015)). Using DSF, the calculated $K_d$ for HSA binding of PFOA was 0.83±0.11 mM (FIGS. 4A-4B), and 0.69±0.03 mM for PFOS (FIGS. 4C-D; Table 3). The calculated $K_d$ for HSA binding of PFOA and PFOS were similar to previously reported values. The findings from the DSF assay and calculated dissociation constant for each PFCA (C4-C12), PFSA (C4-C8), the ether-containing PFAS, (PFAE; FIGS. 4E-4F), and eight fluorotelomer compounds are shown in Table 3. It is notable that the fluorotelomer alcohols 4:2 FTOH and 6:2 FTOH were not bound by HSA and that fluorotelomer compounds with a carboxylate or sulfonate charged group were bound by HSA at affinities similar to those observed for PFAA with the same number of aliphatic carbons (Table 3).

To investigate the sensitivity of the assay to distinguish binding properties for closely related compounds, we compared assay results for HFPO-DA prepared in aqueous buffer or in DMSO containing buffer. In DMSO, HFPO-DA is rapidly converted to E1 via decarboxylation (Liberatore et al. *Environ. Sci. Technol. Lett.* 7, 477-481 (2020)). Two-way ANOVA of the area under the curve of the concentration-response curves for HFPO-DA in DMSO, HFPO-DA in buffer alone (FIG. 4G), and E1 reveals significant differences (F (2.29)=144, p<0.0001), with Tukey's post-hoc analysis indicating that HFPO-DA in DMSO is indistinguishable from the E1 curve with $EC_{50}$ values of 2.34±0.23 mM and 2.36±0.24 mM, respectively (p=0.98; FIG. 4H). Tukey's post-hoc analysis found that HFPO-DA in buffer alone is significantly different from HFPO-DA in DMSO and E1 in buffer (both p<0.0001).

TABLE 3

Binding affinity of HSA for PFAS
Table 3. Binding affinity of HSA for PFAS

| PFCA | CasID | Chain Length | Aliphatic Carbons | Fluorines | $R^2$ | Δ Tm (° C.) | $EC_{50}$ (mM) | Kd (mM) |
|---|---|---|---|---|---|---|---|---|
| PFBA | 375-22-4 | 3 | 4 | 7 | 0.94 | 6.48 ± 0.13 | 2.61 ± 0.19 | 2.57 ± 0.32 |
| PFPeA | 2706-90-3 | 4 | 5 | 9 | 0.97 | 13.1 ± 0.047 | 2.14 ± 0.17 | 2.10 ± 0.23 |
| PFHxA | 307-24-4 | 5 | 6 | 11 | 0.98 | 10.6 ± 0.17 | 1.40 ± 0.11 | 1.64 ± 0.19 |
| PFHpA | 375-85-9 | 6 | 7 | 13 | 0.95 | 15.3 ± 0.29 | 0.68 ± 0.06 | 0.44 ± 0.080 |
| PFOA | 335-67-1 | 7 | 8 | 15 | 0.97 | 13.5 ± 0.29 | 0.84 ± 0.043 | 0.83 ± 0.11 |
| PFNA | 375-95-1 | 8 | 9 | 17 | 0.97 | 13.4 ± 0.24 | 0.60 ± 0.092 | 0.58 ± 0.087 |
| PFDA | 335-76-2 | 9 | 10 | 19 | 0.99 | 17.2 ± 0.09 | 1.11 ± 0.070 | 1.19 ± 0.24 |
| PFunDA | 2058-94-8 | 10 | 11 | 21 | 0.98 | 9.02 ± 0.33 | 1.49 ± 0.024 | 1.36 ± 0.53 |
| PFDoA | 307-55-1 | 11 | 12 | 23 | 0.98 | 7.74 ± 0.14 | 2.51 ± 0.14 | 1.89 ± 0.26 |
| PFSA | | | | | | | | |
| PFBS | 375-73-5 | 4 | 4 | 9 | 0.96 | 11.9 ± 0.08 | 1.72 ± 0.23 | 1.65 ± 0.28 |
| PFHxS | 3871-99-6 | 6 | 6 | 13 | 0.98 | 11.0 ± 0.17 | 0.98 ± 0.028 | 0.71 ± 0.19 |
| PFOS | 2795-39-3 | 8 | 8 | 17 | 0.98 | 16.2 ± 0.63 | 1.13 ± 0.13 | 0.69 ± .032 |
| Per- and Polyfluorinated Alkyl Ethers | | | | | | | | |
| E1 | 3330-15-2 | 5 | 5 | 11 | 0.93 | 7.32 ± 0.042 | 2.34 ± 0.23 | 1.64 ± 0.14 |
| HFPO-DA | 13252-13-6 | 5 | 5 | 11 | 0.97 | 13.7 ± 0.12 | 1.83 ± 0.25 | 1.60 ± 0.16 |
| Nafion bp2 | 749836-20-2 | 7 | 7 | 14 | 0.98 | 12.4 ± 0.12 | 1.90 ± 0.24 | 1.51 ± 0.15 |
| PFO3DoDA | 151772-59-7 | 6 | 7 | 13 | 0.95 | 20.6 ± 0.58 | 1.67 ± 0.19 | 1.53 ± 0.14 |
| Fluorotelomer Alcohols | | | | | | | | |
| 4:2 FTOH | 2043-47-2 | 4 | 6 | 9 | N/A | 0 ± 0 | N/A | N/A |
| 6:2 FTOH | 647-42-7 | 6 | 8 | 13 | N/A | 0 ± 0 | N/A | N/A |
| Fluorotelomer Carboxylic Acids | | | | | | | | |
| 3:3 FTCA | 356-02-5 | 3 | 6 | 7 | 0.81 | 2.24 ± 0.044 | 2.06 ± 0.21 | 1.71 ± 0.19 |
| 5:3 FTCA | 914637-49-3 | 5 | 8 | 11 | 0.94 | 3.62 ± 0.096 | 1.48 ± 0.10 | 0.62 ± 0.042 |
| 6:3 FTCA | 27854-30-4 | 6 | 9 | 13 | 0.95 | 9.50 ± 0.14 | 0.84 ± 0.086 | 0.81 ± 0.092 |
| 8:3 FTCA | 88310-58-1 | 8 | 11 | 17 | 0.89 | 10.01 ± 0.12 | 1.16 ± 0.17 | 0.97 ± 0.068 |
| Fluorotelomer Sulfonic Acids | | | | | | | | |
| 4:2 FTSA | 757124-72-4 | 4 | 6 | 9 | 0.93 | 3.49 ± 0.084 | 1.45 ± 0.14 | 1.07 ± 0.19 |
| 6:2 FTSA | 59587-38-1 | 6 | 8 | 13 | 0.91 | 3.60 ± 0.33 | 0.47 ± 0.12 | 0.37 ± 0.14 |

Chain length is the number of per/poly fluorinated carbons; Δ Tm is 0°, $EC_{50}$ and Kd are mean values reported in ±SEM. Each compound Binding affinities for certain PFAS compounds were also determined using PSA, BSA, and RSA. Results are shown in Table 4. Those findings demonstrate that species specific differences in albumin influence binding properties of each PFAS, and that evaluation of protein binding affinities for protein targets from experimental models or species of interest will be another area of toxicity testing that the DSF assay will be useful. That analysis will be important for accurately extrapolating toxicity testing across species and/or models.

TABLE 4

Binding affinities of albumins for PFAS

| Compound Name | Cas No. | Aliphatic Carbons | Human Kd ± SEM (mM) | Porcine Kd ± SEM (mM) | Bovine Kd ± SEM (mM) | Rat Kd ± SEM (mM) |
|---|---|---|---|---|---|---|
| PFBA | 375-22-4 | 4 | 2.57 ± 0.32 | 1.50 ± 0.11 | 0.98 ± 0.10 | 1.39 ± 0.11 |
| PFHxA | 307-24-4 | 6 | 1.64 ± 0.19 | 1.42 ± 0.03 | 0.95 ± 0.11 | 0.96 ± 0.07 |
| PFOA | 335-67-1 | 3 | 0.83 ± 0.11 | 0.32 ± 0.04 | 0.75 ± 0.05 | ND |
| PFBS | 375-73-5 | 4 | 1.65 ± 0.28 | 1.55 ± 0.04 | 1.13 ± 0.08 | 0.93 ± 0.08 |
| 6:2 FTSA | 59587-38-1 | 8 | 0.37 ± 0.14 | ND | 0.93 ± 0.05 | ND |

Physiochemical Determents of HSA Binding

To interrogate in more detail determinants of HSA binding of PFAS, the relationship between calculated binding affinities, and the number of per- and polyfluorinated carbons, number of aliphatic carbons, or total fluorine numbers for the PFCA series from C4-C12 and across all compounds were analyzed. Except for the PFAE compounds, highest affinity was observed for compounds containing 6-8 fluorinated carbons, 7-9 aliphatic carbons, and containing 13-17 fluorine (FIGS. 5A-5D). For the PFAE, a simple linear regression was more appropriate. For the PFCA series from C4-C12, the best-fit curve for binding affinity by number of per- and polyfluorinated carbons was $=6.30-1.50X+0.10X^2$ (FIG. 5A; $R^2=0.88$) and across all compounds except PFAE was $=4.73-1.08X+0.074X^2$ ($R^2=0.54$). For PFAE, the simple linear regression by per- and polyfluorinated carbons was $=-0.02X+1.7$ (FIG. 5B; $R^2=0.79$). Except for the PFAE, the best-fit curve for the number of aliphatic carbons was $=6.52-1.39X+0.083X^2$ (FIG. 5C; $R^2=0.69$) and by number of fluorine was $=5.35-0.58X+0.019X^2$ (FIG. 5D; $R^2=0.54$). For the PFAE family, the linear regression by number of aliphatic carbons was $==-0.06X+1.9$ (FIG. 5C; $R^2=0.52$) and by number of fluorine was $=-0.01X+1.7$ (FIG. 5D; $R^2=0.77$). Each class is indicated by different colors, with PFCA in red, PFSA in orange, PFAE in green, FTCA in blue, and FTSA in purple. n≥3 across at least two replicate plates for all compounds.

Optimization and Demonstration of Assay Utility

The presented experiments describe the optimization and use of a DSF assay for assessing HSA binding kinetics for control albumin-binding compounds and 24 PFAS from 6 six subclasses. Initial experiments aimed to optimize DSF for measuring PFAS binding included determination of optimal protein and dye concentrations to maximize signal to noise ratio. Those efforts were found especially important for determining albumin binding due to its multiple surface accessible hydrophobic binding sites that increased baseline fluorescence. Additional key factors analyzed during assay development included use of a HEPES buffer to ensure that PFAS with low pKa did not affect assay pH, maintaining consistent ionic strength, determination of appropriate solvents, and optimization of assay temperature ramp rates. Results of those initial experiments identified appropriate conditions for determining the binding affinities of structurally diverse sets of natural fatty acids, small molecule pharmaceuticals, and multiple subclasses of PFAS in a rapid (less than 3 hour) format. The accuracy and reproducibility of the binding affinities calculated using DSF was demonstrated for known albumin-binding drugs warfarin and ibuprofen, C10-C16 fatty acids, PFOA and PFOS. Further demonstrating the utility of this DSF thermal shift approach, comparative evaluation of the HSA binding affinities of structurally diverse subclasses of PFAS revealed that functional groups, number of aliphatic carbons, and number of fluorine bonded to carbons were among the key physiochemical properties that influenced binding.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method comprising:
   (a) providing a first composition comprising a polyfluoroalkyl substance, an environment-sensitive fluorophore, a protein, and an aqueous buffer solution, and determining a melting temperature ($T_m$) for the protein in the first composition, wherein the polyfluoroalkyl substance has a formula:

PFA-X wherein PFA is a perfluoroalkyl group, a perfluoroheteroalkyl group, a polyfluoroalkyl group, or a polyfluoroheteroalkyl group, and X is selected from the group consisting of —COOH, —SO$_3$H, —OH, —SO$_2$NH$_2$, —OC(O)CH=CH$_2$, —OC(O)C(CH$_3$)=CH$_2$, and —CF$_3$;

(b) providing a second composition comprising the environment-sensitive fluorophore, the protein, and the aqueous buffer solution, and determining a melting temperature ($T_m$) for the protein in the second composition; and (c) calculating the difference between the $T_m$ of the protein in the first composition and the $T_m$ of the protein in the second composition ($\Delta T_m$).

2. The method of claim 1, further comprising:

(d) providing N additional compositions, each of which comprises the environment-sensitive fluorophore, the protein, the polyfluoroalkyl substance, and the aqueous buffer solution, wherein N is at least 2, and determining a melting temperature ($T_m$) for the protein in each composition, wherein each additional composition comprises the polyfluoroalkyl substance at a different concentration; and (e) for each of the N additional compositions, calculating the difference between the $T_m$ of the protein in the first composition and the $T_m$ of the protein in each of the N additional compositions ($\Delta T_m$).

3. The method of claim 2, further comprising:

(f) plotting the $\Delta T_m$ for each composition against the concentration of the polyfluoroalkyl substance, and fitting the data to the following equation:

$$Y = \text{Bottom} + \frac{(\text{Top} - \text{Bottom}) * \left(1 - \left(P - Kd - X + \sqrt{(P + X + Kd)^2 - (4*P*X)}\right)\right)}{2*P}$$

wherein:
Top is maximal response;
Bottom is minimal response;
P is protein concentration;
$K_d$ is dissociation constant;
X is polyfluoroalkyl substance concentration; and
Y is $\Delta T_m$;
to thereby determine the dissociation constant for the polyfluoroalkyl substance and the protein.

4. The method of claim 2, further comprising:

(g) plotting the $\Delta T_m$ for each composition against the log-transformed concentration of the polyfluoroalkyl substance, and fitting the data to the following equation:

$$Y = \text{Bottom} + \frac{(\text{Top} - \text{Bottom})}{1 + 10^{\wedge}((\text{Log}EC50 - X) * \text{HillSlope})}$$

wherein:
Top is maximal response;
Bottom is minimal response;
Log$EC_{50}$ is the log-transformed half-maximal effective concentration;
X is ligand concentration;
HillSlope is the Hill coefficient; and
Y is $\Delta T_m$.

5. The method of any claim 1, wherein each $T_m$ is determined by differential scanning fluorimetry.

6. The method of claim 1, wherein each composition is contained within a well of a 96- or 384-well plate.

7. The method of claim 1, wherein the environment-sensitive fluorophore is selected from 9-(2-carboxy-2-cyanovinyl)julolidine, 9-(2,2-dicyanovinyl)julolidine, and 4-(4-(dimethylamino)styryl)-N-methylpyridinium iodide.

8. The method of claim 1, wherein the protein is selected from albumins, fatty acid binding proteins, immunoglobulins, peroxisome proliferator-activated receptors, and thyroid proteins.

9. The method of claim 8, wherein the protein is selected from human serum albumin, bovine serum albumin, porcine serum albumin, rat serum albumin, rabbit serum albumin, and immunoglobulin G.

10. The method of claim 1, wherein the aqueous buffer solution comprises 4-(2-hydroxyethyl)-1-piperazineethanesulfonic acid.

11. The method of claim 1, wherein the polyfluoroalkyl substance is a perfluoroalkylcarboxylic acid, a perfluoroalkylsulfonic acid, a fluorotelomer carboxylic acid, a fluorotelomer sulfonic acid, a fluorotelomer alcohol, a polyfluoroalkyl ether acid, or a perfluoroalkyl ether acid.

12. The method of claim 1, wherein PFA is a $C_1$-$C_{12}$ polyfluoroalkyl group or a $C_1$-$C_{12}$ polyfluoroheteroalkyl group.

13. The method of claim 1, wherein PFA is a $C_1$-$C_{12}$ perfluoroalkyl group or a $C_1$-$C_{12}$ perfluoroheteroalkyl group.

14. The method of claim 1, wherein PFA has a formula:

—(CF$_2$)$_n$CF$_3$, wherein n is 1, 2, 3, 4, 5, 6, 7, 8, 9, 10, or 11.

15. The method of claim 1, wherein PFA has a formula:

—(CH$_2$)$_2$(CF$_2$)$_n$CF$_3$, wherein n is 1, 2, 3, 4, 5, 6, 7, 8, or 9.

16. The method of claim 1, wherein PFA has a formula:

—(CR$^{a1}$R$^{b1}$)$_m$—O—(CC$^{a2}$R$^{b2}$CR$^{a3}$R$^{b4}$O)$_p$—(CR$^{a4}$R$^{b4}$)$_q$—CF$_3$, wherein:
m is 1 or 2;
p is 0, 1, or 2;
q is 0, 1, or 2; and
each R$^{a1}$, R$^{b1}$, R$^{a2}$, R$^{b2}$, R$^{a3}$, R$^{b3}$, R$^{a4}$, and R$^{b4}$ is independently selected from F, CF$_3$, and H.

17. The method of claim 1, wherein X is —COOH, —SO$_3$H, —OH, or —CF$_3$.

18. The method of claim 1, wherein the first and/or second composition further comprises a water-miscible organic solvent selected from dimethylsulfoxide, methanol, ethanol, N,N-dimethylformamide, and a polyethylene glycol.

19. A composition comprising:
an environment-sensitive fluorophore, a protein, a polyfluoroalkyl substance, and an aqueous buffer solution, wherein the polyfluoroalkyl substance has a formula:

PFA-X wherein PFA is a perfluoroalkyl group, a perfluoroheteroalkyl group, a polyfluoroalkyl group, or a polyfluoroheteroalkyl group, and X is selected from the group consisting of —COOH, —SO₃H, —OH, —SO₂NH₂, —OC(O)CH=CH₂, —OC(O)C(CH₃)=CH₂, and —CF₃.

* * * * *

UNITED STATES PATENT AND TRADEMARK OFFICE
CERTIFICATE OF CORRECTION

PATENT NO. : 12,392,782 B2
APPLICATION NO. : 17/704825
DATED : August 19, 2025
INVENTOR(S) : Scott M. Belcher and Thomas W. Jackson Page 1 of 1

It is certified that error appears in the above-identified patent and that said Letters Patent is hereby corrected as shown below:

In the Claims

In Claim 5, Column 22, Line 1:
"The method of any claim 1, wherein each $T_m$ is"
Should read:
-- The method of claim 1, wherein each $T_m$ is --
And
Claim 16, Column 22, Lines 42-44:
"The method of claim 1, wherein PFA has a formula:
$-(CR^{a1}R^{b1})_m\text{-}O\text{-}(CC^{a2}R^{b2}CR^{a3}R^{b4}O)_p\text{-}(CR^{a4}R^{b4})_q\text{-}CF_3$,"
Should read:
-- The method of claim 1, wherein PFA has a formula:
$-(CR^{a1}R^{b1})_m\text{-}O\text{-}(CR^{a2}R^{b2}CR^{a3}R^{b4}O)_p\text{-}(CR^{a4}R^{b4})_q\text{-}CF_3$, --

Signed and Sealed this
Twenty-fifth Day of November, 2025

John A. Squires
*Director of the United States Patent and Trademark Office*